United States Patent [19]

Sherrod et al.

[11] Patent Number: 5,558,734
[45] Date of Patent: Sep. 24, 1996

[54] METHOD OF MANUFACTURING INCONTINENCE ARTICLE FOR MALES

[75] Inventors: Earle H. Sherrod, Appleton; Lynn K. LeMahieu, Hortonville; John A. Rooyakkers, Little Chute, all of Wis.

[73] Assignee: Kimberly-Clark Corporation, Neenah, Wis.

[21] Appl. No.: 440,048

[22] Filed: May 12, 1995

Related U.S. Application Data

[62] Division of Ser. No. 164,340, Dec. 9, 1993.

[51] Int. Cl.$^6$ ............ A61F 13/15; A61F 13/56; B32B 31/08; B32B 31/10
[52] U.S. Cl. .......... 156/164; 156/163; 156/269; 156/299; 156/300; 156/301; 156/302; 604/385.1; 604/385.2; 604/387
[58] Field of Search ............ 604/358, 373, 604/385.1, 385.2, 394, 387; 156/163–164, 229, 264, 265, 269, 299–302, 494–496

[56] References Cited

U.S. PATENT DOCUMENTS

| D. 263,169 | 2/1982 | Larko . |
|---|---|---|
| D. 271,800 | 12/1983 | Brendling . |
| D. 287,282 | 12/1986 | Ternström . |
| D. 294,972 | 3/1988 | Nicklasson . |
| D. 298,566 | 11/1988 | Runeman . |
| 2,538,758 | 1/1951 | Bricmont . |
| 3,406,690 | 10/1968 | Igel et al. . |
| 3,441,025 | 4/1969 | Ralph . |
| 3,522,808 | 8/1970 | Worcester . |
| 3,583,402 | 6/1971 | Cordell et al. . |
| 3,920,019 | 11/1975 | Shaar . |

(List continued on next page.)

FOREIGN PATENT DOCUMENTS

| 0140478 | 5/1985 | European Pat. Off. . |
|---|---|---|
| 0155515A1 | 9/1985 | European Pat. Off. . |
| 0167931A2 | 1/1986 | European Pat. Off. . |
| 0231974A1 | 8/1987 | European Pat. Off. . |
| 0324502 | 7/1989 | European Pat. Off. . |
| 0376022 | 7/1990 | European Pat. Off. . |
| 0442223 | 8/1991 | European Pat. Off. . |
| 0439962A1 | 8/1991 | European Pat. Off. . |
| 0450541A2 | 10/1991 | European Pat. Off. . |
| 2572649 | 5/1986 | France . |
| 2677541 | 12/1992 | France . |
| 2142243 | 1/1985 | United Kingdom . |
| 2165755 | 4/1986 | United Kingdom . |
| 2182840 | 5/1987 | United Kingdom . |
| 2268073 | 1/1994 | United Kingdom . |
| WO85/03428 | 8/1985 | WIPO . |
| 86/05387 | 9/1986 | WIPO . |
| 86/06620 | 11/1986 | WIPO . |
| WO86/06621 | 11/1986 | WIPO . |
| WO8707136 | 12/1987 | WIPO . |
| WO91/07156 | 5/1991 | WIPO . |
| WO91/07155 | 5/1991 | WIPO . |
| WO92/01431 | 2/1992 | WIPO . |
| WO92/15269 | 9/1992 | WIPO . |

*Primary Examiner*—Adrienne C. Johnstone
*Attorney, Agent, or Firm*—Thomas M. Gage

[57] ABSTRACT

Absorbent articles of the present invention are specifically adapted for the adult male anatomy. The articles include a moisture barrier having a length measured between front and back ends of less than about 46 centimeters. A liner is bonded to the moisture barrier sandwiching an absorbent assembly therebetween. The moisture barrier is gathered along each of its side edges between forward and rearward terminal points. The forward terminal points are spaced from the front end of the moisture barrier by at least about 7 centimeters, and the rearward terminal points spaced from the back end of the moisture barrier by less than about 5 centimeters. Elasticized containment flaps disposed on the liner extend longitudinally toward the front end to a position at least about 16 centimeters from the back end of the moisture barrier. The moisture barrier is also gathered along its back end. In particular embodiments, a retaining member is bonded to the liner and defines therebetween a compartment having a volume of at least about 25 cubic centimeters, and a cover formed of a liquid impermeable material is bonded to the liner.

9 Claims, 7 Drawing Sheets

U.S. PATENT DOCUMENTS

| | | |
|---|---|---|
| 4,197,849 | 4/1980 | Bostick . |
| 4,340,563 | 7/1982 | Appel et al. . |
| 4,388,075 | 6/1983 | Mesek et al. . |
| 4,405,297 | 9/1983 | Appel et al. . |
| 4,453,938 | 6/1984 | Brendling . |
| 4,505,706 | 3/1985 | Erpicum et al. . |
| 4,559,051 | 12/1985 | Hanson . |
| 4,560,380 | 12/1985 | Tharel . |
| 4,576,599 | 3/1986 | Lipner . |
| 4,578,073 | 3/1986 | Dysart et al. . |
| 4,579,556 | 4/1986 | McFarland . |
| 4,589,878 | 5/1986 | Mitrani . |
| 4,590,760 | 7/1986 | Buell . |
| 4,590,931 | 5/1986 | Kidwell, Jr. . |
| 4,597,761 | 7/1986 | Buell . |
| 4,601,716 | 7/1986 | Smith . |
| 4,601,717 | 7/1986 | Blevins . |
| 4,627,846 | 12/1986 | Ternström . |
| 4,643,726 | 2/1987 | Gegelys . |
| 4,662,877 | 5/1987 | Williams . |
| 4,668,229 | 5/1987 | Fago et al. . |
| 4,668,230 | 5/1987 | Damico et al. . |
| 4,675,012 | 6/1987 | Rooyakkers . |
| 4,681,577 | 7/1987 | Stern et al. . |
| 4,685,914 | 8/1987 | Holtman . |
| 4,701,177 | 10/1987 | Ellis et al. . |
| 4,704,116 | 11/1987 | Enloe . |
| 4,710,188 | 12/1987 | Runeman . |
| 4,725,468 | 2/1988 | McIntyre . |
| 4,731,063 | 3/1988 | Newkirk . |
| 4,731,065 | 3/1988 | Yamada . |
| 4,731,070 | 3/1988 | Koci . |
| 4,770,657 | 9/1988 | Ellis et al. . |
| 4,772,280 | 9/1988 | Rooyakkers . |
| 4,772,282 | 9/1988 | Oakley . |
| 4,795,450 | 1/1989 | Tovar et al. . |
| 4,798,603 | 1/1989 | Meyer et al. . |
| 4,846,823 | 7/1989 | Enloe . |
| 4,846,825 | 7/1989 | Enloe et al. . |
| 4,865,597 | 9/1989 | Mason, Jr. et al. . |
| 4,886,509 | 12/1989 | Mattsson . |
| 4,886,512 | 12/1989 | Damico et al. . |
| 4,892,536 | 1/1990 | DesMarais et al. . |
| 4,925,520 | 5/1990 | Beaudoin et al. . |
| 4,938,754 | 7/1990 | Mesek . |
| 4,940,464 | 7/1990 | Van Gompel et al. . |
| 4,944,735 | 7/1990 | Mokry . |
| 4,946,454 | 8/1990 | Schmidt . |
| 5,013,309 | 5/1991 | Baigas, Jr. et al. . |
| 5,019,070 | 5/1991 | Ruben . |
| 5,032,121 | 7/1991 | Mokry . |
| 5,074,853 | 12/1991 | Bryant . |
| 5,074,856 | 12/1991 | Coe et al. . |
| 5,129,893 | 7/1992 | Thorén . |
| 5,246,431 | 9/1993 | Minetola et al. . |
| 5,356,405 | 10/1994 | Thompson et al. . |
| 5,413,654 | 5/1995 | Igaue et al. ........................ 156/164 X |
| B1 4,315,508 | 11/1988 | Bolick . |

METHOD OF MANUFACTURING INCONTINENCE ARTICLE FOR MALES

This is a divisional application of copending Application U.S. Ser. No. 08/164,340, filed on Dec. 9, 1993.

BACKGROUND OF THE INVENTION

The present invention v-elates generally to the field of absorbent articles. More particularly, the invention pertains to a disposable absorbent article adapted specifically for use by male wearers, and a method of making such an article.

Urine incontinence is a serious concern for many individuals. While the incidence of urine incontinence is greater for females than males, many men as well suffer at one time or another from urine incontinence.

Nevertheless, the majority of incontinence products have not been designed specifically for males. Rather, most incontinence products have been formed similar to conventional diapers, in that they are generally planar, rectangular or hourglass shaped, and sized to receive both urine and feces. Such urine and excrement collecting devices have several disadvantages. In particular, they are designed to handle additional waste than what is necessary for persons who solely require a urine-collecting device. Consequently, such products sacrifice comfort by occupying space between the legs of the wearer and extending up to the small of the back, and as a result such products are often too bulky for discreet protection. The wearer may, simply by sitting, shift the position of the product and/or reduce the absorbent potential of the product.

Recently, urine specific products in the form of pads and guards have become available. These products desirably provide discreet incontinence protection in a comfortable fashion. Lacking specific accommodation for the male anatomy, however, these products are more suited for females.

Most male-specific products that have been provided to date have included stocking-shaped sheaths with an insertion opening. Below the opening is a cone-shaped pocket lined with absorbent material. The penis or penis and scrotum of the wearer are inserted through the opening and reside in the pocket. Such sheath devices may present obvious disadvantages. For example, to avoid leakage, the edge portions of the opening often close tightly against the skin in the area around the penis. The result is either a lack of comfort or a risk of leakage. Further, the penis and possibly the scrotum as well are surrounded by absorbent material. This can result in an unpleasant sensation of dampness after urination and skin irritation from exposure to urine.

What is lacking and needed in the art is an absorbent article suitable for use by males that provides a dry environment for the penis and scrotum, addresses the needs of urine-only incontinent individuals, and is shaped so that it is comfortable and discreet to wear and tailored to fit the adult male anatomy.

SUMMARY OF THE INVENTION

In response to the discussed difficulties and problems encountered in the prior art, a new disposable absorbent article has been developed. Absorbent articles of the present invention comfortably contain the male genitalia, reduce leakage and promote dryness. In one embodiment, an absorbent article of the present invention has longitudinal and transverse axes and includes a moisture barrier formed of a liquid impermeable material. The moisture barrier defines a front end, a back end longitudinally spaced from the front end, and a pair of side edges extending between the front and back ends. The moisture barrier has a length measured between the front and back ends of less than about 46 centimeters. The absorbent article also includes an absorbent assembly and a liner formed of a liquid permeable material. The liner is bonded to the moisture barrier to sandwich the absorbent assembly therebetween. The moisture barrier is gathered along each side edge between forward and rearward terminal points. The forward terminal points are spaced from the front end of the moisture barrier by at least about 7 centimeters, and the rearward terminal points are spaced from the back end of the moisture barrier by less than about 5 centimeters. A pair of elasticized containment flaps are disposed on the liner so that each containment flap extends longitudinally toward the front end to a position at least about 10 centimeters from the back end of the moisture barrier. The moisture barrier is also gathered along its back end.

This aspect of the invention yields a relatively short article that is targeted for urine incontinence. In use, the back end of the article is positioned adjacent the perineum of the wearer so that the wearer generally does not sit on the article. Thus, the absorbent assembly is less subject to bunching and twisting during use. The article is gathered along the sides near the back end and along the back end to form a cupped region in which the scrotum of the wearer resides. Also, the penis of the wearer is maintained over the absorbent assembly by the elastic containment flaps.

In another embodiment, an absorbent article of the present invention generally includes a moisture barrier formed of a liquid impermeable material. The moisture barrier defines a front end, a back end and a pair of side edges, and has a length of from about 18 to about 46 centimeters. A liner formed of a liquid permeable material is bonded to the moisture barrier to sandwich an absorbent assembly therebetween. A retaining member of the absorbent article is bonded to the liner and defines therebetween a compartment having a volume of at least about 25 cubic centimeters. An opening to the compartment is located within about 20 centimeters of the back end of the moisture barrier, and the compartment extends from the opening toward the front end at least about 5 centimeters. Longitudinal gathering members are operatively joined to the moisture barrier along each side edge and are longitudinally offset toward the back end of the moisture barrier. A transverse gathering member is operatively joined to the moisture barrier along its back end.

In particular embodiments, the absorbent article also includes a cover formed of a liquid impermeable material and bonded to the liner. The cover has a surface area of at least about 13 square centimeters, is positioned longitudinally between the retaining member and the back end of the moisture barrier, and extends longitudinally inward from the back end by at least about 4 centimeters.

This aspect of the invention provides an especially dry environment for the wearer. The retaining member holds the penis of the wearer in its proper position, while the cover protects against leakage past the back end of the abbreviated article. The penis is held in the compartment with the scrotum resting on the cover.

Another aspect of the invention pertains to efficient methods for making disposable absorbent articles. A method of the present invention includes: providing a continuous web of liquid impervious moisture barrier material, where this moisture barrier web has a machine direction and a transverse direction; disposing a plurality of absorbent assemblies on the moisture barrier web; bonding a continuous web of liquid permeable liner material to the moisture barrier web, this liner web sandwiching the absorbent assemblies between the liner web and the moisture barrier web; stretch bonding a plurality of longitudinal gathering members to the moisture barrier web, each longitudinal gathering member having a long dimension extending generally parallel to the machine direction of the moisture barrier web; stretch bonding a plurality of transverse gathering members to the moisture barrier web, each transverse gathering member having a long dimension of at least about 8 centimeters and a width dimension of at least about 3 centimeters, the long dimension extending parallel to the transverse direction of the moisture barrier web; and transversely cutting the assembly of the moisture barrier, liner web, and longitudinal and transverse gathering members web at spaced locations to form a series of individual absorbent articles and divide each transverse gathering member into front and back portions. The method is carried out so that each individual absorbent article has longitudinally spaced front and back ends and side edges extending between the front and back ends; each individual absorbent article has a length measured between the front and back ends of less than about 46 centimeters and a longitudinal gathering member along each side edge, the longitudinal gathering members of each individual absorbent article are longitudinally offset toward the back end; and the back portion of each transverse gathering member constitutes more than 55 percent of the width dimension of the transverse gathering member.

As can be seen from the foregoing, an absorbent article of the present invention provides urine-only incontinent individuals a dry environment for the penis and scrotum, in a cupped structure that is comfortable and discreet to wear. Articles of the invention can be efficiently manufactured.

Numerous other benefits and advantages of the present invention will appear from the following description. In the description, reference is made to the accompanying drawings which illustrate preferred embodiments of the invention. Such embodiments do not represent the full scope of the invention. Reference should therefore be made to the claims herein for interpreting the full scope of the invention.

DEFINITIONS

Within the context of this specification, each term or phrase below will include the following meaning or meanings:

(a) "bonded" refers to the joining, adhering, connecting, attaching, or the like, of two elements. Two elements will be considered to be bonded together when they are bonded directly to one another or indirectly to one another, such as when each is directly bonded to intermediate elements.

(b) "disposable" includes being disposed of after use, and not intended to be washed and reused.

(c) "disposed", "disposed on", "disposed with", "disposed at", "disposed near", and variations thereof are intended to mean that one element can be integral with another element, or that one element can be a separate structure joined to or connected to or placed with or placed near another element.

(d) "elastic," "elasticized" and "elasticity" include that property of a material by virtue of which it tends to recover its original size and shape after removal of a force causing the deformation.

(e) "liquid communication" means that liquid is able to pass between the specified layers.

(f) "force" includes a physical influence exerted by one body on another which produces acceleration of bodies that are free to move and deformation of bodies that are not free to move. Force is expressed in grams per unit area.

(g) "front" and "back" are used to designate relationships relative to the garment itself and not necessarily any position the garment assumes when it is positioned on a wearer.

(h) "gathered" and "gatherable" refer to a material that is or can be drawn together such as in pleats or folds.

(i) "member" when used in the singular can have the dual meaning of a single element or a plurality of elements.

(j) "operatively joined", with reference to the attachment of an elastic member to another element, means that the elastic member when attached to or connected to the element, or treated with heat, gives the element elastic properties; and with reference to the attachment of a non-elastic member to another element, means that the member and element can be attached in any suitable manner that permits or allows them to perform the intended or described function of the joinder. The, joining, attaching, connecting or the like can be either directly, such as joining either member directly to an element, or can be indirectly by means of another member disposed between the first member and the first element.

(k) "outward" refers to a position relative to the center of an absorbent article, and particularly transversely and/or longitudinally away from the longitudinal and transverse center of the absorbent article.

(l) "stretch bonded" refers to an elastomeric strand being bonded to another member while said elastomeric strand is elongated at least about 25 percent of its relaxed length. Desirably, the term "stretch bonded" refers to the situation wherein the elastomeric strand is elongated at least about 100 percent, more desirably at least about 300 percent, of its relaxed length when it is bonded to the other member.

(m) "stretch bonded laminate" refers to a composite material having at least two layers in which one layer is a gatherable layer and the other layer is an elastic layer. The layers are joined together when the elastic layer is in a stretched condition so that upon relaxing the layers, the gatherable layer is gathered. (n) "tension" includes a uniaxial force tending to cause the extension of a body or the balancing force within that body resisting the extension.

These definitions are not intended to be limiting, and these terms may be defined with additional language in the remaining portion of the specification.

DETAILED DESCRIPTION OF THE PREFERRED EMBODIMENTS

Figure 1:
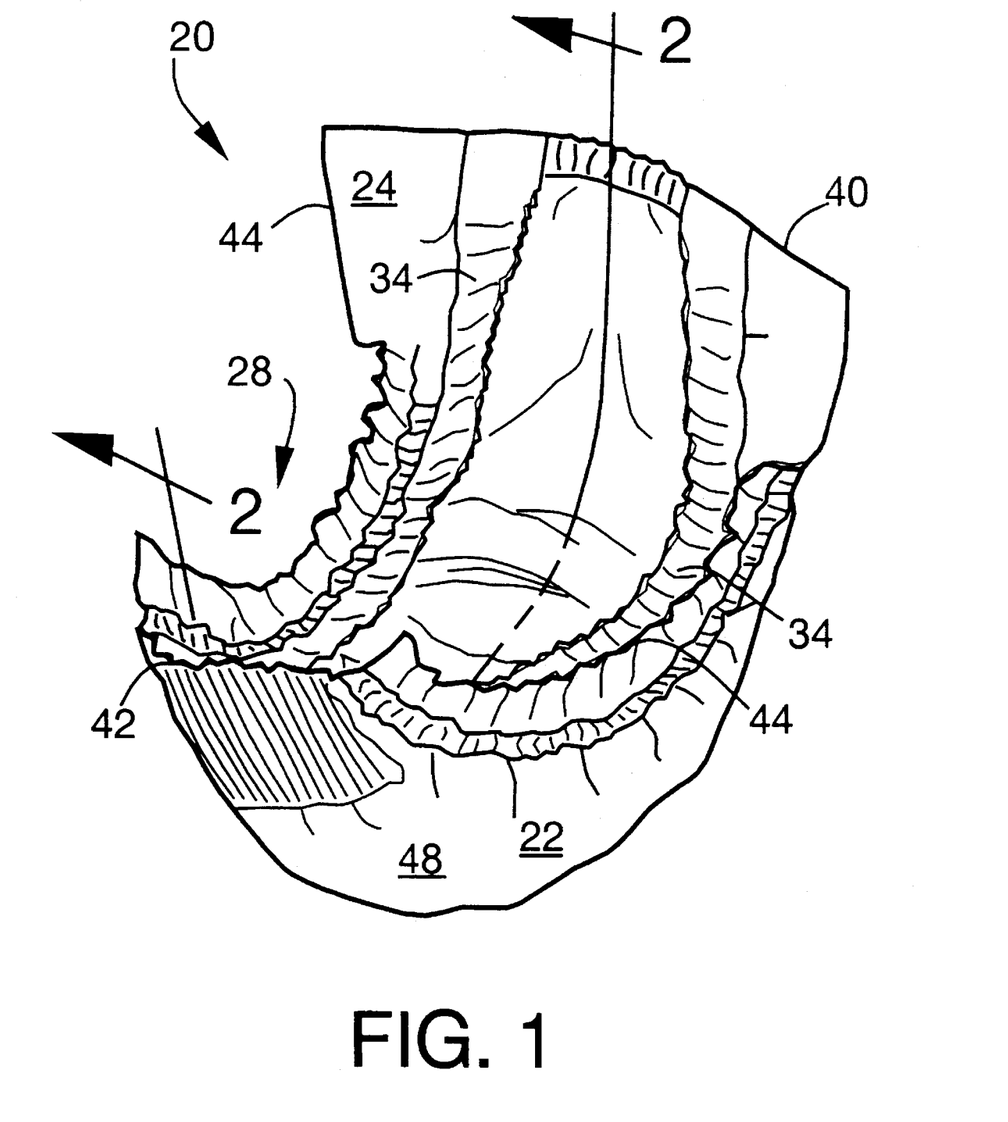
FIG. 1 is a perspective view of a disposable absorbent article according to the present invention.
Figure 2:
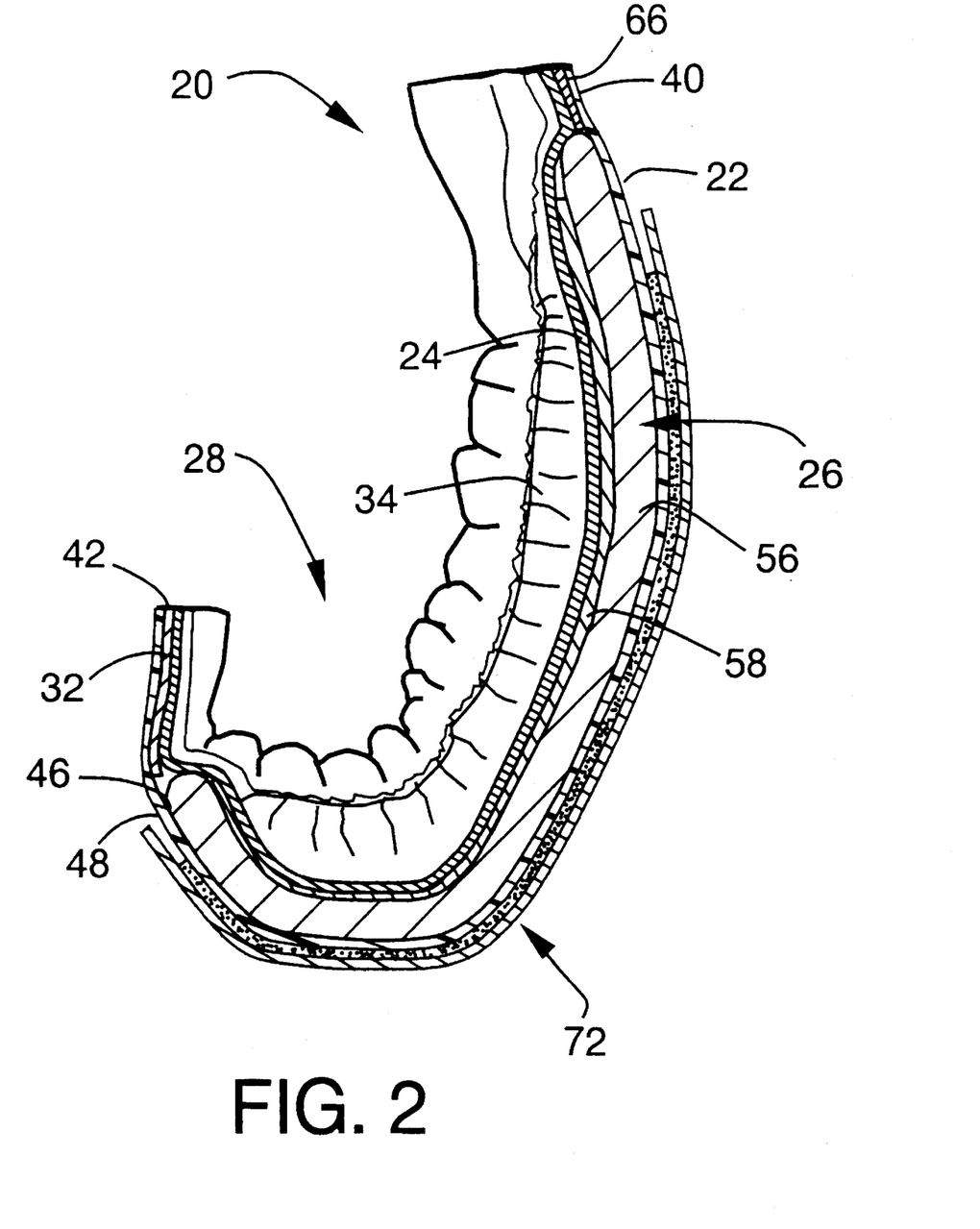
FIG. 2 is an enlarged longitudinal section view taken generally from the plane of the line 2—2 in FIG. 1.
Figure 3:
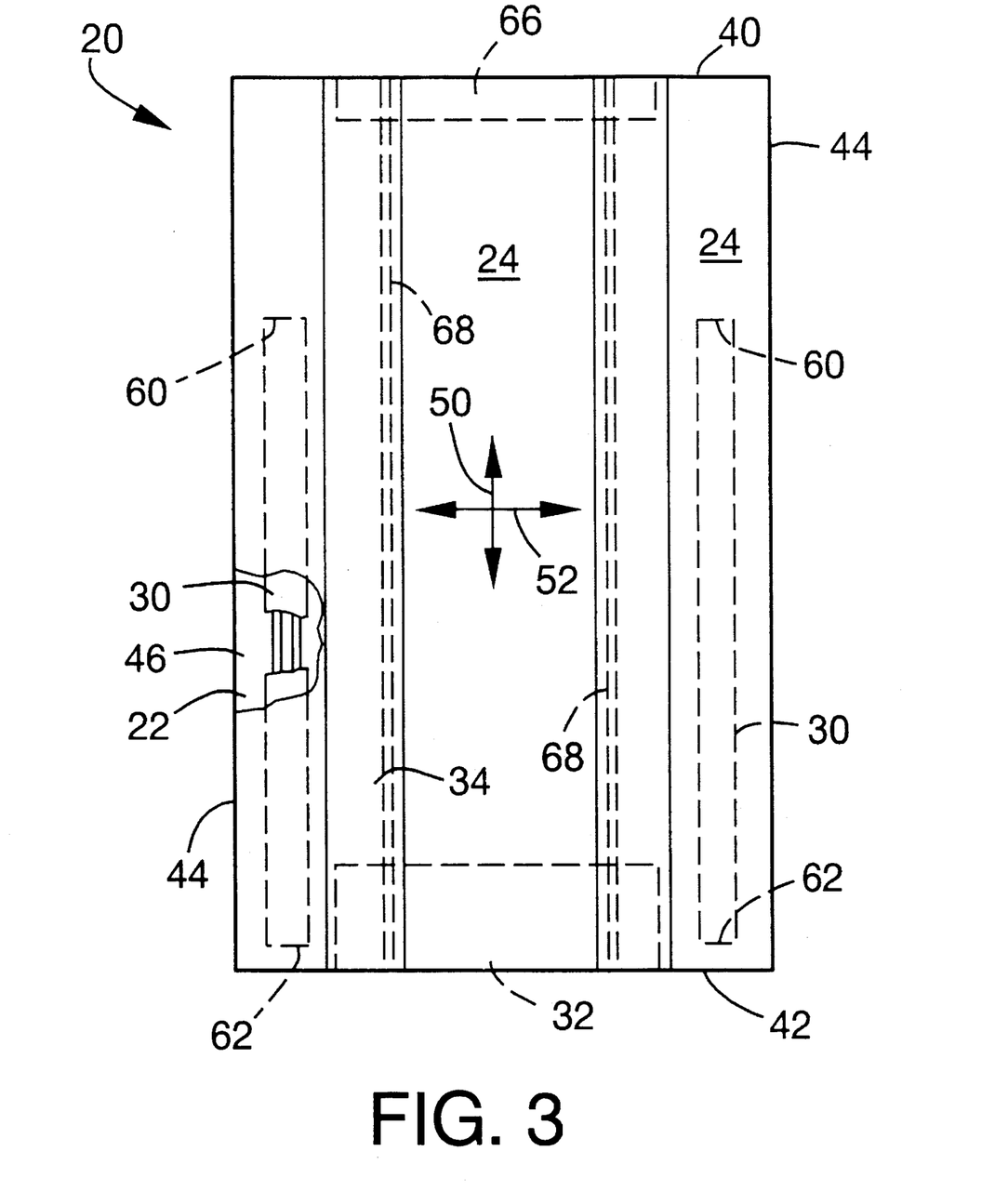
FIG. 3 is a top plan view of the disposable absorbent article shown in FIG. 1, shown in a flat and stretched condition.

One embodiment of a disposable absorbent article 20 according to the present invention is shown in FIGS. 1–3. The absorbent article 20 is specifically designed to address urinary incontinence and be compatible with the adult male anatomy. In general, the absorbent article 20 includes a moisture barrier 22, a bodyside liner 24, and an absorbent assembly 26 (FIG. 2) sandwiched between the moisture barrier and liner. The article 20 has a body-conforming cupped region 28 at one end FIGS. 1 and 2) as a result of the interaction between two longitudinal gathering members 30 and a transverse gathering member 32 (FIG. 3). A pair of containment flaps 34 maintain the penis of the wearer in proper position relative to the absorbent article 20 and minimize leakage. The components of the urinary incontinence article 20 will now be described in more detail.

The moisture barrier 22 is desirably formed from a flexible, gatherable material that is substantially liquid impermeable. The moisture barrier 22 has a front end 40, a back end 42 longitudinally spaced from the front end, and a pair of side edges 44 extending between the front and back ends. The moisture barrier 22 also has opposite major surfaces designated inner surface 46 and outer surface 48.

For the absorbent article 20 to be worn forward of the perineum, the moisture barrier 22 suitably has a length of from about 18 to about 46 centimeters, desirably from about 25 to about 41 centimeters, and particularly about 38 centimeters. The length of the moisture barrier 22 is measured along the outer surface 48 between the front and back ends 40 and 42, parallel to the longitudinal axis 50 of the article (FIG. 3). Where the moisture barrier 22 is gathered, such as by an elastic material, the length is measured with the moisture barrier in a generally flat and stretched condition.

The moisture barrier 22 suitably has a width in the range of from about 10 to about 25 centimeters, and particularly about 20 centimeters. The width of the moisture barrier 22 is measured along the outer surface 48 between the side edges 44, parallel to the transverse axis 52 of the article. Where the moisture barrier 22 is gathered, the width is measured in a generally flat and stretched condition. The width of the moisture barrier 22 may but need not narrow toward the back end 42. Regardless of the width of the moisture barrier 22, however, the Resulting Width of the absorbent article 20 desirably narrows toward the back end 42, as described in greater detail below.

The absorbent assembly 26 (FIG. 2) is disposed on the inner surface 46 of the moisture barrier 22 and is desirably sufficiently flexible to readily conform to the contour of the inner surface. The absorbent assembly 26 may be bonded to the inner surface 46 using adhesives or other suitable means.

The absorbent assembly 26 is sized to be shorter and narrower than the moisture barrier 22, and may be T-shaped, I-shaped, rectangular or irregularly-shaped. By way of example, the absorbent assembly 26 may be rectangular with a length in the range of about 8 to about 36 centimeters, particularly about 31 centimeters, and a width in the range of about 1 to about 19 centimeters, particularly about 13 centimeters.

The absorbent assembly 26 comprises a liquid storage layer 56 formed of a material adapted to absorb and retain urine, and optionally, an acquisition layer 58 (FIG. 2). The absorbent assembly 26 is generally configured according to the amount of liquid intended to be absorbed, and the absorbent rate and capacity of the assembly components. In particular, the storage layer 56 suitably has a capacity of urine of from about 50 to 300 grams, particularly about 150 grams. The urine capacity of the storage layer 56 is its saturated retention capacity, which is a measure of the total absorbent capacity of an absorbent garment, material or structure.

Saturated retention capacity of the storage layer 56 may be determined as follows. The material to be tested, having a moisture content of less than about 7 weight percent, is weighed and submerged in an excess quantity of room temperature (about 23 degrees Celsius) synthetic urine. The material to be tested is allowed to remain submerged for 20 minutes. After 20 minutes, the material is removed ing 0.25 inch openings (commercially available from Taconic Plastics Inc., Petersburg, N.Y.) which, in turn, is placed on a vacuum box and covered with a flexible rubber dam material. A vacuum of 3.5 kilopascals (0.5 pounds per square inch ) is drawn in the vacuum box for a period of 5 minutes. The material is weighed. The amount of fluid retained by the material being tested is determined by subtracting the dry weight of the material from the wet weight of the material (after application of the vacuum) and is reported as the saturated retention capacity in grams of fluid retained. For relative comparisons, this value can be divided by the weight of the material to give the saturated retention capacity in grams of fluid retained per gram of tested material.

The synthetic urine composition referenced herein comprises 0.31 grams monobasic calcium phosphate monohydrate ($CaH_4(PO_4)_2H_2O$), 0.68 grams monobasic potassium phosphate ($KH_2PO_4$), 0.48 grams magnesium sulphate heptahydrate ($MgSO_4\ 7H_2O$), 1.33 grams potassium sulphate $K_2SO_4$), 1.24 grams tribasic sodium phosphate dodecahydrate ($Na_3PO_4\ 12H_2O$), 4.4 grams sodium chloride (NaCl), 3.16 grams potassium chloride (KCl). 8.56 grams of urea ($CO(NH_2)_2$), 0.1 grams Pluronic 10R8 surfactant (a nonionic surfactant commercially available from BASF-Wyandotte Corporation) and 1 gram methyl paraben and 1 gram Germall 115 preservative (commercially available from Santell Chemical Company, Chicago, Ill.) per liter using distilled water as the solvent. The components are added to 900 milliliters of distilled water in the order given and each dissolved before the next component is added. The solution is finally diluted to one liter.

If material, such as high-absorbency material or fiber is drawn through the fiberglass screen while on the vacuum box, a screen having smaller openings should be used. Alternatively, a piece of tea bag material can be placed between the material and the screen and the final value adjusted for the fluid retained by the tea bag material. Suitable tea bag material is a heat sealable tea bag material grade 542, commercially available from Kimberly-Clark Corporation. The amount of fluid absorbed by the tea bag material is determined by performing the saturated retention capacity test on an empty tea bag. Testing high-absorbency materials or fibers alone can be accomplished using a sealed pouch of tea bag material.

In one embodiment, the liquid storage layer 56 comprises an airlaid batt of wood pulp fluff and high absorbency materials, as hereinafter described. The storage layer 56 may have a thickness of from about 0.2 to about 1 centimeter, such as about 0.5 centimeter, and a density of from about 0.1 to about 0.3 grams per cubic centimeter, such as about 0.18 grams per cubic centimeter.

The acquisition layer 58 is superposed on top of and in liquid communication with the storage layer 56. Dots or lines of adhesives, ultrasonic bonds or other suitable means may be employed to bond the acquisition layer 58 to the storage layer 56. The acquisition layer 58 may be generally the same size and shape as the storage layer 56.

The acquisition layer 58 can be or can contain any suitable material for managing, transporting, accommodating, permitting, or directing rapid and/or sudden flow of urine therethrough and into contact with the storage layer 56. The acquisition layer 58 desirably functions to draw liquid from the liner 24 and then permit desorption by the storage layer 56. One suitable material for the acquisition layer 58 is a latex bonded polyester, which is available from Sackner Products of Grand Rapids, Mich. under the trade designation SH-66. Other suitable materials are disclosed in U.S. Pat. No. 4,798,603 issued Jan. 17, 1989, to Meyer et al., which is incorporated herein by reference.

The liner 24, which is formed of a substantially liquid permeable material, is positioned to sandwich the absorbent assembly 26 between the liner and the moisture barrier 22. The liner 24 and moisture barrier 22 may be bonded together longitudinally and transversely outward from the absorbent assembly 26 using thermal bonds, adhesives, ultrasonic bonds or other suitable means. Alternately, the liner 24 may be bonded to or about the absorbent assembly 26 (not shown). In either case, the liner 24 desirably covers at least a portion of the absorbent assembly 26. In an alternate embodiment, the liner 24 is positioned directly over the storage layer 56 and the acquisition layer 58 is bonded to the surface of the liner that is remote from the storage layer 56 (not shown).

The longitudinal gathering members 30 operate together with the transverse gathering men, bet 32 to form the cupped region 28 particularly suited for male wearers. The longitudinal gathering members 30 comprise an elastic material operatively joined to the moisture barrier 22 along each side edge 44. As illustrated, each longitudinal gathering member 30 includes a plurality of individual elastic strands stretch bonded between a strip of gatherable nonwoven material and the inner surface 46 of the moisture barrier 22 (see FIG. 3). The longitudinal gathering members 30 when in a relaxed state function to gather the moisture barrier 22 along the side edges 44. The longitudinal gathering members 30 may be operatively joined, for example stretch bonded, directly to the moisture barrier 22, the liner 24, or both.

Rather than being centered between the front and back ends 40 and 42, the longitudinal gathering members 30 are longitudinally offset toward the back end 42 of the moisture barrier 22. Each longitudinal gathering member 30 has forward and rearward terminal points 60 and 62, which represent the functional ends of the elastic material (FIG. 3). The terminal points 60 and 62 may be the physical ends of the elastic material, as illustrated, where the full length of the elastic material causes a gathering of the moisture barrier 22. Alternately, the terminal points may simply represent the forwardmost and rearwardmost locations at which the elastic material is bonded to the moisture barrier 22 (not shown).

In the illustrated embodiment, the cupped region 28 is formed between the longitudinal center of the absorbent article 20 and the back end 42, and the region near the front end 40 of the article 20 is generally ungathered so as to lie flat against the abdomen of the wearer. Accordingly, the forward terminal points 60 are desirably spaced from the front end 40 by at least about 7 centimeters, and particularly at least about 10 centimeters, such as about 11 centimeters. Additionally, the forward terminal points 60 are desirably spaced from the back end 42 by less than about 40 centimeters, and particularly less than about 30 centimeters. At the other end, the rearward terminal points 62 are desirably spaced from the back end 42 by less than about 8 centimeters, desirably less than about 5 centimeters, and particularly less than about 2 centimeters.

The transverse gathering member 32 comprises an elastic material operatively joined to the moisture barrier 22 along the back end 42. The transverse gathering member 32 may, for instance, be stretch bonded directly to the moisture barrier 22. The transverse elastic member 32 desirably has a long dimension measuring at least about 8 centimeters, such as about 13 centimeters, and a width dimension measuring at least about 1 centimeter, such as at least about 3 centimeters. As illustrated in FIG. 3, the long dimension is positioned to extend parallel to the transverse axis 52 of the article 20, such that the moisture barrier 22 is gathered and stretchable along the back end 42.

To facilitate formation of the cupped region 28, the rearward terminal points 62 of the longitudinal gathering members 30 are desirably located within about 6 centimeters, and particularly within about 2 centimeters, of the transverse gathering member 32. The transverse gathering member 32 may also function to provide a barrier to liquid flow past the back end 42 of the article 20. To promote such an upstanding physical barrier, the absorbent assembly 26 is desirably positioned longitudinally inward from the transverse gathering member 32. The positioning of the transverse gathering member 32 longitudinally between the absorbent assembly 26 and the back end 42 is illustrated in FIG. 2.

The absorbent article 20 may optionally also include a front elastic member 66 operatively joined to the moisture barrier 22 along the front end 40. As suggested by FIG. 1, it is desirable for the front elastic member 66 to provide a reduced amount of transverse gathering force as compared to the transverse gathering member 32, which is located along the back end 42. As a result, the article 20 has a Resulting Width that narrows toward the back end 42. The Resulting Width is the distance measured parallel to the transverse axis 52 between the side edges 44, with the elastic in a relaxed condition. One efficient way of accomplishing this is for the transverse gathering member 32 and front elastic member 66 to be formed of the same material and I have the same long dimension length, but for the transverse gathering member to have a width dimension that is greater than that of the front elastic member.

The longitudinal gathering members 30 and the transverse gathering member 32 are each illustrated as separate elastic materials that are bonded to the moisture barrier 22. These gathering members 30 and 32 could also be formed by treating, for example heat treating, portions of the moisture barrier 22 to give them elastic properties. The gathering members could also be formed by pleating, a single elastic material of which the gathering members are integral portions, or other suitable means.

The pair of containment flaps 34 of the illustrated absorbent article 20 are disposed on the liner 24 and extend generally the full length of the article. The containment flaps 34 include one or more elastic strands 68 (FIG. 3) which cause the containment flaps to stand upright relative to the liner 24. The containment flaps 34 may be attached to the liner 24 using adhesives, ultrasonic bonds, thermal bonds or other suitable means, or formed from the liner. Desirably, however, the containment flaps 34 are separately formed of a substantially liquid impermeable nonwoven material folded upon itself with the elastic strands 68 enclosed therein and attached to the liner 24. Containment flaps 34 suitable for use in the present invention may be formed as disclosed in U.S. Pat. Nos. 4,704,116 issued Nov. 11, 1987, and 4,846,823 issued Jul. 11, 1989, to Enloe, which are incorporated herein by reference.

The upstanding containment flaps 34 maintain the penis of the wearer in proper position over the transverse center region of the article 20 and thus over absorbent assembly 26. Because the back end 42 of the article 20 resides adjacent the perineum of the wearer, the containment flaps 34 desirably extend longitudinally toward the front end 40 to a position at least about 10 centimeters from the back end 42. This assures that for a wide variety of male sizes the flaps 34 will be positioned to maintain the penis over the absorbent assembly 26. The flaps 34 also provide a barrier to lateral liquid movement, which is particularly significant at locations longitudinally forward of the forward terminal points 60 of the longitudinal gathering members 30. Additionally, the containment flaps 34 assist in forming a pocket for the scrotum of the wearer in the cupped region 28 of the absorbent article 20. Consequently, the containment flaps 34 desirably extend longitudinally toward the back end 42 to a position less than about 3 centimeters from the back end, and particularly to the back end.

The absorbent article 20 may also include attachment means 72 (FIG. 2), for example garment attachment adhesive and a strip of release paper, to secure the moisture barrier 22 to underclothing of the wearer.

Figure 4:
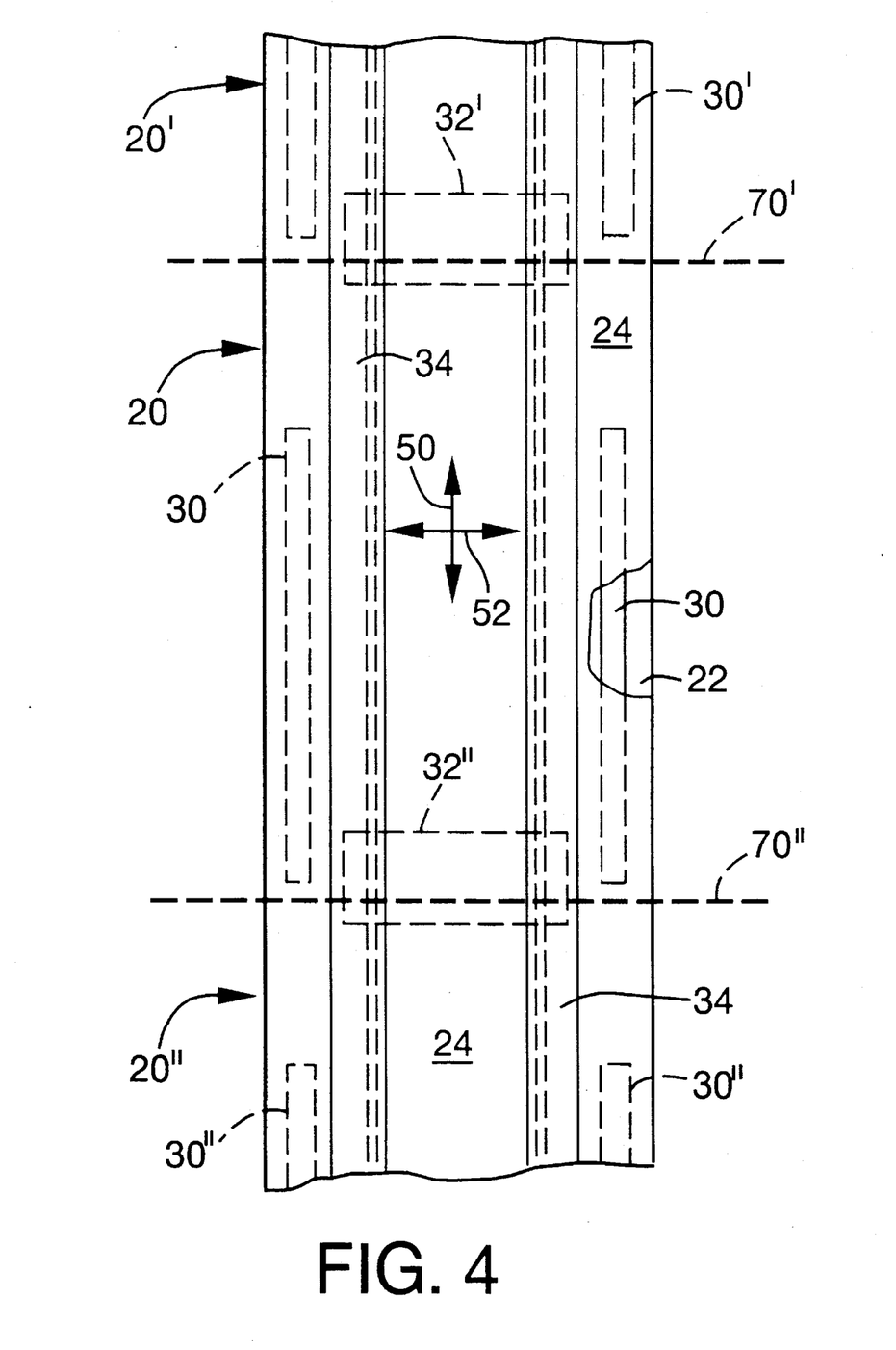
FIG. 4 is a schematic representation of an intermediate stage of assembly of the absorbent articles shown in FIG. 1.

The absorbent article 20 may be constructed by separately forming each element and uniting them as identified above. Alternately, absorbent articles 20 of the invention may be manufactured in a continuous process where the component materials are transported along the machine direction of a manufacturing line, bonded together, and cut to form a series of individual absorbent articles. An assembly of components during a stage of manufacture is illustrated in FIG. 4, where the individual articles are designated 20, 20' and 20".

In the process, a continuous web of moisture barrier material 22 is transported such that the longitudinal axis 50 of each resulting absorbent article is parallel to the machine direction. A continuous web of liner material 24 is bonded to the moisture barrier web 22 with a plurality of absorbent assemblies 26 (not shown in FIG. 4) sandwiched between the liner web and moisture barrier web.

Additionally, a plurality of longitudinal gathering members 30, 30' and 30" are stretch bonded to the moisture barrier web 22. The long dimension of each longitudinal gathering member 30, 30' and 30" is positioned to extend generally parallel to the longitudinal axis of the moisture barrier web 22. Alternately, continuous elastic strands or ribbons could be sandwiched between the liner web 24 and moisture barrier web 22 and only bonded between the terminal point positions 60 and 62 noted above.

Also, a plurality of transverse gathering members 32' and 32" are stretch bonded to the moisture barrier web 22. Each transverse gathering member 32' and 32" defines a long dimension and a width dimension. The long dimension is positioned to extend parallel to the transverse direction of the moisture barrier web 22. The width dimension is thereby positioned to extend parallel to the machine direction of the moisture barrier web 22.

The moisture barrier web 22, liner web 24, longitudinal gathering members 30, 30' and 30" and transverse gathering members 32' and 32" form an assembly of components that is then transversely cut at spaced locations, such as cutting lines 70' and 70" in FIG. 4. The cutting lines divide the assembly into the individual absorbent articles 20, 20' and 20" and define the front and back ends 40 and 42 of each article.

The position of the cutting lines 70' and 70" may be readily adjusted to provide each absorbent article with both a front elastic member 66 and a transverse gathering member 32 as illustrated in FIG. 3. Specifically, the cutting lines 70' and 70" may be spaced to divide each transverse gathering member 32' and 32" into front and back portions, where the back portion of each transverse gathering member 32' and 32" constitutes more than 55 percent, and particularly at least about 75 percent, of the width dimension of the transverse gathering member. The front portion, which forms the front elastic member 66, will provide a reduced amount of transverse gathering force as compared to the back portion, which forms the transverse gathering member 32.

In use, the absorbent article 20 is positioned on the wearer with the front end 40 adjacent the abdomen of the wearer and the back end 42 adjacent the perineum. The scrotum of the wearer tends to reside in the cupped region 28, due to the cup shape formed by the combination of the longitudinal and transverse gathering members 30 and 32 and the presence of the containment flaps 34 in the cupped region. The penis is located forward of the cupped region and is maintained over the absorbent assembly 26 by the elasticized containment flaps 34.

With the back end 42 of the article 20 located adjacent the perineum, the wearer can be seated without sitting on a major absorbent portion of the article 20. This enhances comfort and minimizes compression of the absorbent. The transverse gathering member 32 also gives the article 20 a relatively narrow Resulting Width at the back end 42 so that it can more comfortably fit between the legs of the wearer. At the other end, the front region is relatively ungathered compared to the cupped region 28. This allows the front region to lie relatively flat against the wearer's abdomen, providing a form of discreetness. Urine is quickly absorbed by the absorbent assembly 26, with side leakage minimized by the containment flaps 34.

Figure 5:
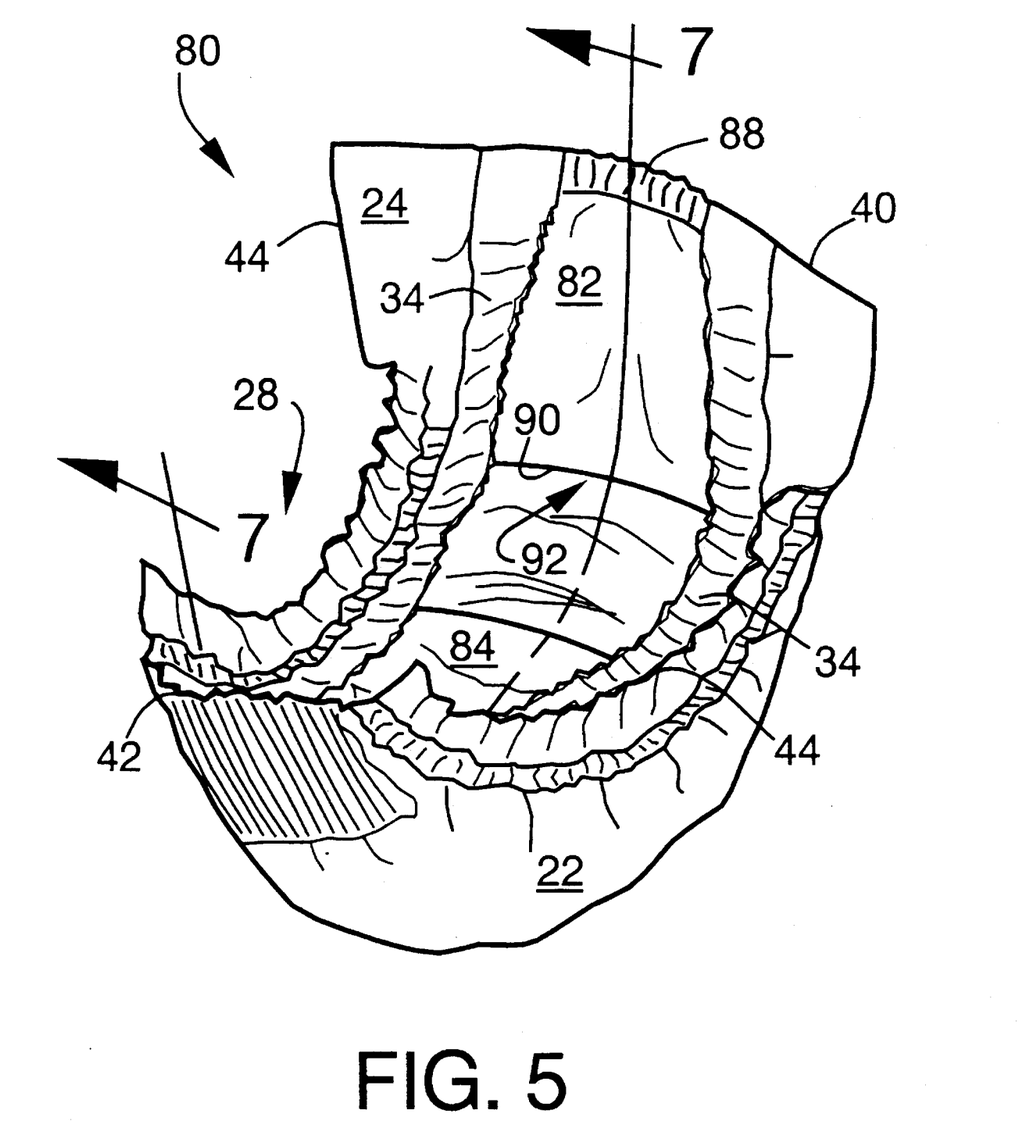
FIG. 5 is a perspective view of an alternate disposable absorbent article according to the present invention.
Figure 6:
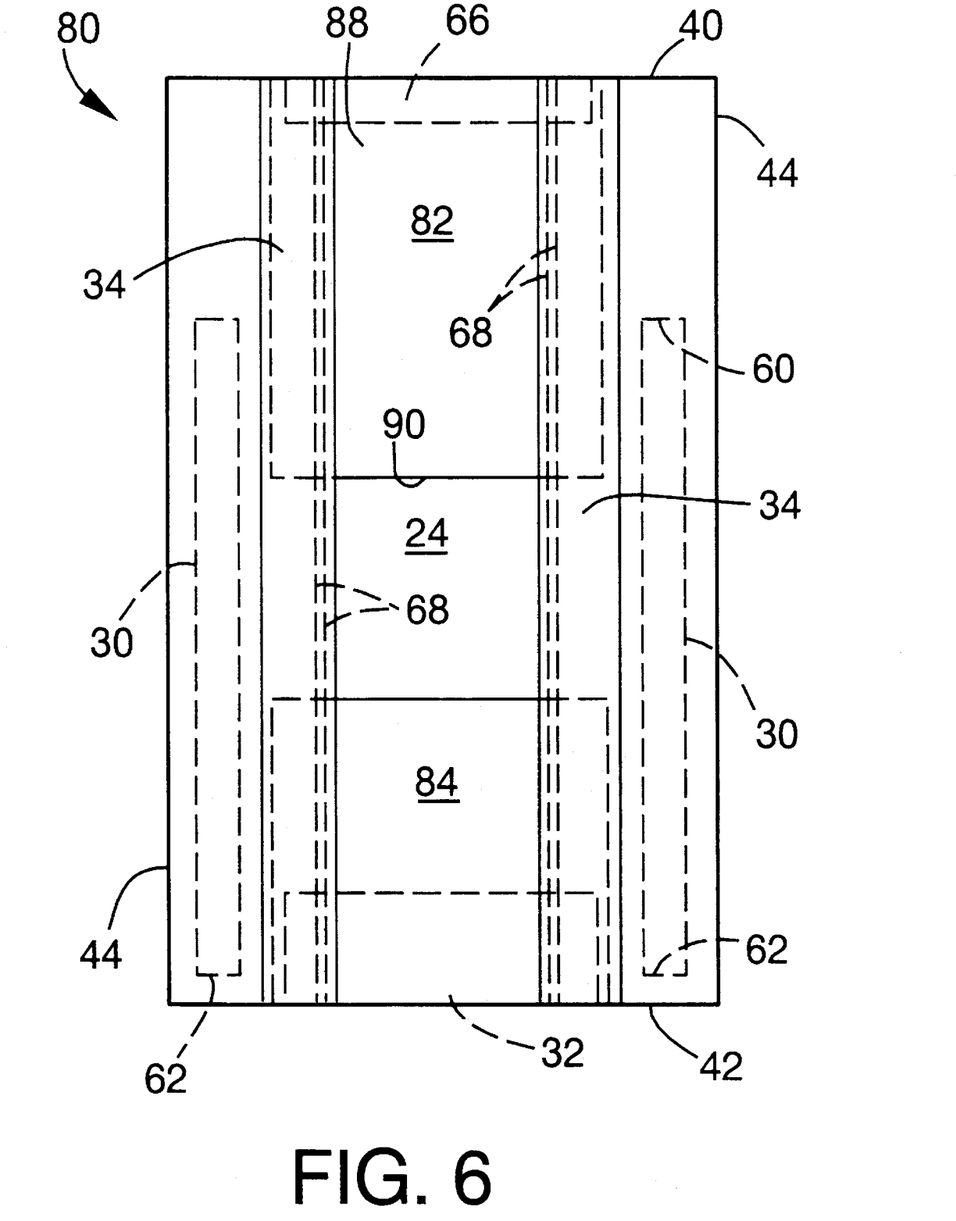
FIG. 6 is a top plan view of the disposable absorbent article shown in FIG. 5, shown in a flat and stretched condition.
Figure 7:
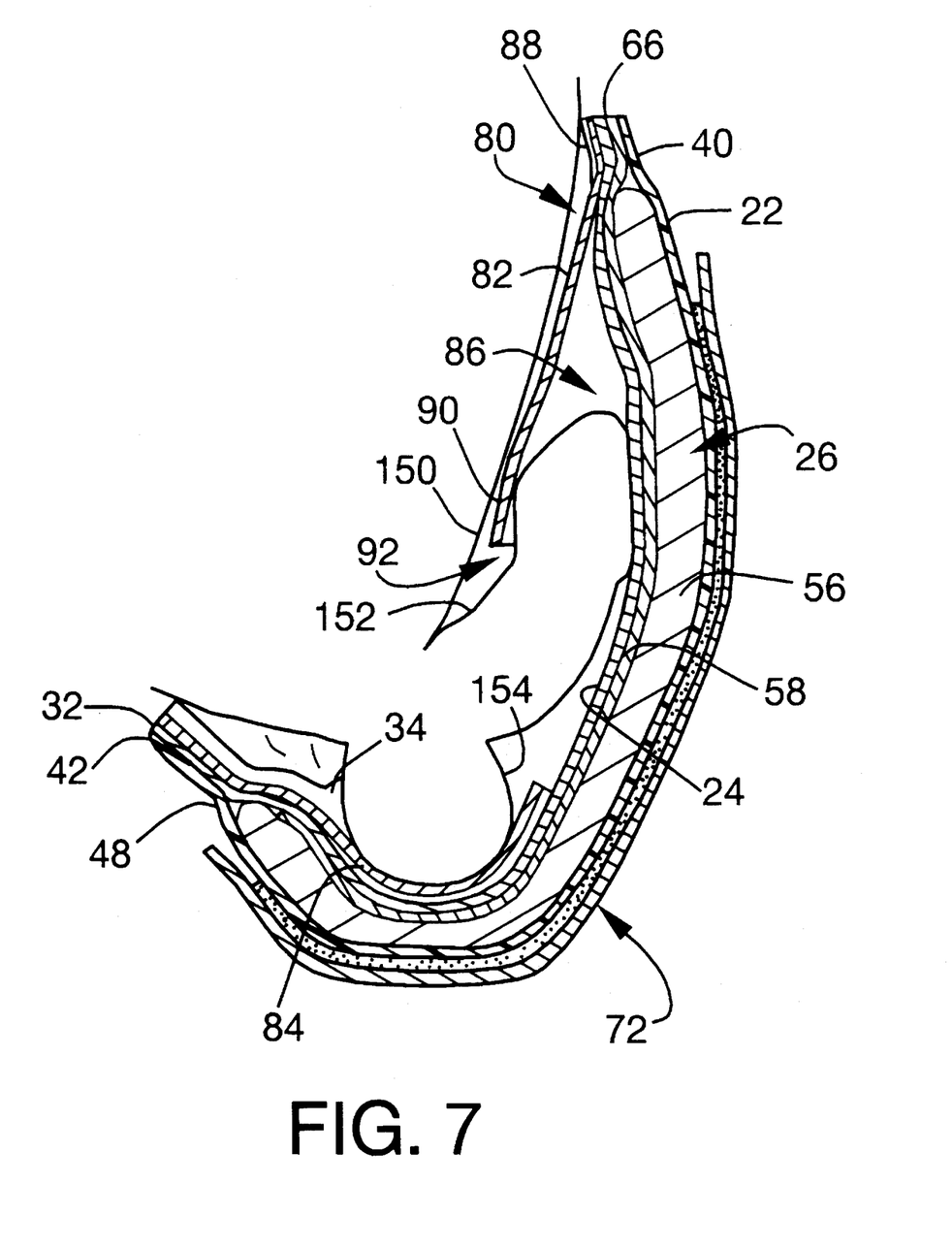
FIG. 7 is an enlarged longitudinal section view taken generally from the plane of the line 7—7 in FIG. 5, and including a representation of the male anatomy while the article is in use.

An alternate absorbent article 80 according to the present invention is illustrated in FIGS. 5–7, where components similar to those previously described have been given the same reference numeral. The absorbent article 80 represents a modification of the article 20 of FIGS. 1–3 by incorporation of a retaining member 82 and a cover 84. Both the retaining member 82 and cover 84 may be separately formed and bonded to the assembly of components illustrated in FIG. 4 (not shown).

As in the previously-described embodiment, the absorbent article 80 includes a moisture barrier 22 having a front end 40, a back end 42 and side edges 44. A liner 24 is bonded to the moisture barrier 22 and sandwiches an absorbent assembly 26 (FIG. 7) between the liner and moisture barrier. Longitudinal gathering members 30 (FIG. 6) are operatively joined to the moisture barrier 22 along each side edge 44 and desirably offset toward the back end 42. A transverse gathering member 32 (FIG. 6) is operatively joined to the moisture barrier 22 along the back end 42, and a front elastic member 66 may optionally be provided along the front end 40. The resulting article 80 has a cupped region 28 toward the back end 42, and may also include a pair of elasticized containment flaps 34.

The retaining member 82 is attached to the liner 24 such that it defines a compartment 86 (FIG. 7) for retaining the penis of the wearer in the proper position over the absorbent assembly 26 during use. The retaining member 82 desirably comprises a material that is vapor permeable and liquid impermeable. Suitable materials include films, nonwovens, laminates of films and nonwovens, or the like. For example, the retaining member 82 may be or comprise a cast or blown film formed of polypropylene, polyethylene, or the like, or a gas permeable thermal laminate comprising a polyethylene film and a polypropylene spunbond web.

The retaining member 82 may be generally rectangular in shape with a first end 88, an opposite second end 90, and sides extending between the first and second ends. The first end 88 and the sides are desirably bonded to the liner 24 using thermal bonds, adhesives, ultrasonic bonds or other suitable means. The second end 90 remains unattached to the liner, however, thereby defining an opening 92 (FIGS. 5 and 7) or point of entry to the compartment 86.

The retaining member 82 is desirably sized so that the sides are positioned adjacent or beneath the containment flaps 34. Further, the first end 88 is desirably positioned adjacent the front end 40. To fit a range of males, the unattached second end 90 and thus the opening 92 are desirably located within about 20 centimeters, more desirably within about 16 centimeters, from the back end 42 of the moisture barrier 22. Further, the retaining member 82 and thus the compartment 86 extend from the opening 92 toward the front end 40 at least about 5 centimeters, desirably at least about 10 centimeters, and more desirably all the way to the front end. Accordingly, the retaining member 82 desirably has a surface area of from about 90 to about 210 square centimeters, and particularly about 180 square centimeters.

The compartment 86 represents generally the volume beneath the retaining member 82, such as between the retaining member and the liner 24, that is available for the penis. The compartment 86 may have a volume of from about 25 to about 245 cubic centimeters, particularly about 125 cubic centimeters. The volume of the compartment 86 may be determined by estimating, based on physical measurement, the average dimensions of the compartment, or by another suitable method.

The cover 84 is attached to the liner 24 at the back end 42 of the absorbent article 80 to minimize or prevent leakage from the back end and to keep the scrotum of the wearer dry. The cover 84 may be bonded to the liner 24 at spaced locations or over its full surface area using thermal bonds, adhesives, ultrasonic bonds or other suitable means. The cover 84 desirably extends longitudinally inward from the back end 42 by at least about 4 centimeters, and particularly about 8 centimeters, and has a surface area of from about 13 to about 194 square centimeters, particularly about 70 square centimeters.

The cover 84 may be formed of a material that is substantially liquid impermeable and vapor permeable. Suitable materials may be or comprise a nonwoven web or cast or blown film formed of polypropylene, polyethylene, or the like, or a gas permeable thermal laminate comprising a polyethylene film and a polypropylene spunbond web.

The absorbent article 80 is illustrated in use in the enlarged longitudinal section view of FIG. 7. The article 80 is positioned on a male torso 150 such that the front 40 is toward the front of the wearer and the back end 42 is adjacent the perineum. The penis 152 of the wearer is inserted into the opening 92 to reside in the compartment 86, while the scrotum 154 of the wearer resides against the cover 84. In addition to the features and advantages noted above in relation to the embodiment of FIGS. 1–3, the retaining member 82 assists in keeping the article 80 in a proper position in relation to the penis, both before and during urination without pressing tightly against the skin. The penis is maintained near the absorbent assembly 26, and urine is prevented from escaping by the moisture barrier 22, retaining member 82 and cover 84. In both embodiments, the articles 20 and 80 provide sufficient air flow around the penis and scrotum by not surrounding them with absorbent material. Also, the acquisition layer 58 and cover 84 (article 80) serve to keep the skin of the wearer dry after urination.

A wide variety of materials may be used to construct the aforementioned components of the absorbent articles 10 and 80. Numerous examples of materials used in constructing absorbent articles are described in the aforementioned U.S. patents incorporated by reference herein.

The moisture barrier 22 desirably comprises a flexible, gatherable material that is substantially liquid impermeable. An exemplary material suitable for use in forming the moisture barrier 22 is a thin, substantially liquid impermeable web or sheet of plastic film such as polyethylene, polypropylene, polyvinyl chloride or similar material having a thickness of about 1.0 to about 1.5 millimeter. Alternately, the moisture barrier 22 may comprise a nonwoven, fibrous web which has been suitably constructed and arranged to be substantially liquid impermeable. Still alternately, the moisture barrier 22 may comprise a layered or laminated material, such as a thermally bonded plastic film and nonwoven web composite.

The liner 24 may be any soft, flexible, porous sheet which passes fluids therethrough. The liner 24 may comprise, for example, a nonwoven web or sheet of wet strength tissue paper, a spunbonded, meltblown or bonded-carded web composed of synthetic polymer filaments, such as polypropylene, polyethylene, polyesters or the like, or a web of natural polymer filaments such as rayon or cotton. The liner 24 has a pore size that readily allows the passage therethrough of liquids, such as urine and other body exudates. The liner 24 may be selectively embossed or perforated with discrete slits or holes extending therethrough, such as an apertured film material. Optionally, the web or sheet may be treated with a surfactant to aid in liquid transfer. One preferred liner material is a wettable spunbonded polypropylene having a basis weight of 0.7 ounces per square yard. Such material may be produced by the methods and apparatus described in U.S. Pat. Nos. 4,340,563 and 4,405,297 to Appel et al., which are incorporated herein by reference.

The storage layer 56 is desirably an air-formed batt of cellulosic fibers (i.e., wood pulp fluff). One preferred type of wood pulp fluff, which is available under the trade designation CR1654 from Kimberly-Clark Corporation of Neenah, Wis., U.S.A., is a bleached, highly absorbent sulphate wood pulp containing softwood fibers. Optionally, the storage layer 56 could comprise a conform material composed of a mixture of cellulosic fibers and synthetic polymer fibers. For example, the conform material may comprise an airlaid blend of cellulosic wood fibers and meltblown polyolefin fibers, such as polyethylene or polypropylene fibers.

The storage layer 56 may also include compounds to increase its absorbency, such as an effective amount of organic or inorganic high-absorbency materials. For example, the storage layer 56 can include 0–95 weight percent high-absorbency material. Suitable inorganic high-absorbency materials include, for example, absorbent clays and silica gels. Organic high-absorbency materials can include natural materials, such as pectin, guar gum and peat moss, as well as synthetic materials, such as synthetic hydrogel polymers. Such hydrogel polymers may include, for example, carboxymethylcellulose, alkali metal salts of polyacrylic acids, polyacrylamides, polyvinyl alcohol, ethylene maleic anhydride copolymers, polyvinyl ethers, hydroxypropyl cellulose, polyvinyl morpholinone, polymers and copolymers of vinyl sulfonic acid, polyacrylates, polyacrylamides, polyvinyl pyridine or the like. Other suitable polymers can include hydrolyzed acrylonitrile grafted starch, acrylic acid grafted starch, and isobutylene maleic anhydride copolymers, and mixtures thereof. The hydrogel polymers are preferably sufficiently cross-linked to render the materials substantially water-insoluble. Cross-linking may, for example, be by irradiation or by covalent, ionic, van der Waals, or hydrogen bonding. Suitable materials are available from various commercial vendors, such as Dow Chemical Company, Hoechst Celanese Corporation, and Allied Colloids, Inc. Typically, the high-absorbency material is capable of absorbing at least about 15 times its weight in water, and preferably is capable of absorbing more than about 25 times its weight in water.

The high-absorbency material can be distributed or otherwise incorporated into the storage layer 56 employing various techniques. For example, the high-absorbency material can be substantially uniformly distributed among the fibers comprising the storage layer. The materials can also be nonuniformly distributed within the storage layer fibers to form a generally continuous gradient with either an increasing or decreasing concentration of high-absorbency material, as determined by observing the concentration moving inward from the moisture barrier 22. Alternatively, the high-absorbency material can comprise a discrete layer separate from the fibrous material of the storage layer 56, or can comprise a discrete layer integral with the storage layer.

The storage layer 56 may also include a tissue wrap layer to help maintain the integrity of the fibrous core. This tissue wrap typically comprises a hydrophilic cellulosic material, such as creped wadding or a high wet-strength tissue.

Included among suitable components for acquisition layer 58 are substantially hydrophobic transport materials such as nonwoven polypropylene, polyethylene, polyester, blends thereof, or the like. The acquisition layer 58 may contain or be treated with a suitable surfactant to increase its initial wettability in adjustment of the performance of this invention. When treated with a surfactant, however, the acquisition layer 58 should still be less hydrophilic than the storage layer 56. The presence of an effective amount of surfactant on the acquisition layer 58 can advantageously increase the rate of movement of liquid into the storage layer 56 during initial insult of urine. After the initial insult, however, bodily discharges such as urine will continue to move through the acquisition layer 58 whether or not the surfactant is present therein. Accordingly, the surfactant may be water dispersible, if desired. Various surfactants are available, with one suitable surfactant being identified as Triton X-102 and available from Rohm and Haas Corporation of Philadelphia, Pa.

The acquisition layer 58 may have a substantially uniform density throughout and an essentially or generally nonlayered configuration. The density, for instance, can be from about 0.015 to about 0.5 grams per cubic centimeter, and the thickness can be from about 0.3 to about 1.3 centimeters, such as about 0.6 centimeters. The acquisition layer may have a fiber denier from about 1.5 to about 15, and particularly from about 1.5 to about 6. The acquisition layer 58 may also have a pore size gradient therein, for instance, as having a series of stratified zones, or may have a substantially uniform porosity.

The elastic gathering members 30 and 32 and the front elastic member 66 may be formed of a dry-spun coalesced multifilament elastomeric thread sold under the tradename LYCRA and available from I.E. Du Pont de Nemours and Company. Alternately, the elastic members may be formed of other typical elastics utilized in the diaper-making art, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 22 and the liner 24. Other suitable elastic gathering means are disclosed in U.S. Pat. No. 4,938,754 to Mesek and 4,388,075 to Mesek et al.

The foregoing detailed description has been for the purpose of illustration. Thus, a number of modifications and changes may be made without departing from the spirit and scope of the present invention. For instance, alternative or optional features described as part of one embodiment can be used to yield another embodiment. Additionally, two named components could represent portions of the same structure. For example, the retaining member 82 or cover 84 could be formed by a portion of the moisture barrier 22 folded over the absorbent assembly 26, or the cover 84 could be formed by a portion of the liner 24 being treated to be substantially liquid impermeable. Therefore, the invention should not be limited by the specific embodiments described, but only by the claims.

We claim:

1. A method of making an absorbent article, comprising the steps of:

providing a continuous moisture barrier web of liquid impervious moisture barrier material, the moisture barrier web having a machine direction and a transverse direction;

disposing a plurality of absorbent assemblies on the moisture barrier web;

bonding a continuous liner web of liquid permeable liner material to the moisture barrier web, the liner web sandwiching the absorbent assemblies between the liner web and the moisture barrier web;

stretch bonding a plurality of longitudinal gathering members to the moisture barrier web, each longitudinal gathering member having a long dimension extending generally parallel to the machine direction of the moisture barrier web;

stretch bonding a plurality of transverse gathering members to the moisture barrier web, each transverse gathering member having a long dimension of at least about 8 centimeters and a width dimension of at least about 3 centimeters, the long dimension extending parallel to the transverse direction of the moisture barrier web; and transversely cutting the assembly of the moisture barrier web, the liner web, and the longitudinal and transverse gathering members at spaced locations to form a series of individual absorbent articles and divide each transverse gathering member into front and back portions;

wherein each individual absorbent article has longitudinally spaced front and back ends and side edges extending between the front and back ends, each individual absorbent article has a length measured between the front and back ends of less than about 46 centimeters and a longitudinal gathering member along each side edge, the longitudinal gathering members of each individual absorbent article are longitudinally offset toward the back end, and the back portion of each transverse gathering member constitutes more than 55 percent of the width dimension of the transverse gathering member.

2. The method of claim 1, further comprising the step of bonding a retaining member for each absorbent article to the liner web to define therebetween a compartment having an opening located within about 20 centimeters of the back end, the compartment extending from the opening toward the front end at least about 5 centimeters and having a volume of at least about 25 cubic centimeters.

3. The method of claim 2, further comprising the step of bonding a liquid impermeable cover for each absorbent article to the liner web, the cover longitudinally positioned between the retaining member and the back end and extending longitudinally inward from the back end by at least about 4 centimeters, the cover having a surface area of at least about 13 square centimeters.

4. The method of claim 1, wherein the longitudinal gathering members of each individual absorbent article have forward and rearward terminal points, the forward terminal points being spaced from the front end by at least about 7 centimeters and the rearward terminal points being spaced from the back end by less than about 5 centimeters.

5. The method of claim 4, wherein the forward terminal points are spaced from the front end by at least about 10 centimeters.

6. The method of claim 4, wherein the rearward terminal points are located within about 6 centimeters of the back end transverse gathering member.

7. The method of claim 6, wherein the rearward terminal points are located within about 2 centimeters of the back end transverse gathering member.

8. The method of claim 1, further comprising the step of disposing a pair of continuous elasticized containment flaps on the liner web.

9. The method of claim 8, wherein in each individual absorbent article each containment flap extends longitudinally toward the back end to a position less than about 3 centimeters from the back end and toward the front end to a position at least about 10 centimeters from the back end.

* * * * *